United States Patent [19]

Böckmann et al.

[11] 4,016,190

[45] Apr. 5, 1977

[54] PROCESS FOR THE PREPARATION OF DIARYLCARBONATES

[75] Inventors: August Böckmann; Claus Wulff; Hugo Vernaleken; Wolfgang Alewelt, all of Krefeld; Uwe Hucks, Alpen, all of Germany

[73] Assignee: Bayer Aktiengesellschaft, Germany

[22] Filed: Feb. 26, 1976

[21] Appl. No.: 661,528

[30] Foreign Application Priority Data

Mar. 1, 1975 Germany .......................... 2509036

[52] U.S. Cl. .............................................. 260/463
[51] Int. Cl.$^2$ ...................................... C07C 68/02
[58] Field of Search .................................... 260/463

[56] References Cited

UNITED STATES PATENTS 3,382,207  5/1968  Jaquiss .............................. 260/463

FOREIGN PATENTS OR APPLICATIONS 1,056,141  4/1957  Germany .......................... 260/463
1,227,144  3/1968  United Kingdom .............. 260/463
1,324,763  3/1971  United Kingdom .............. 260/463

Primary Examiner—Lewis Gotts
Assistant Examiner—D. R. Phillips
Attorney, Agent, or Firm—Connolly and Hutz

[57] ABSTRACT

A process for the preparation of a symmetric diarylcarbonate by reacting phosgene with a phenol wherein said reactions is carried out by the phase interface process in a diphastic mixture of an aqueous alkali metal hydroxide solution and a liquid diaryl carbonate in the presence of from 0.001 to 0.1 mol of a tertiary amine or a quaternary ammonium compound per mol of phenol.

13 Claims, No Drawings

PROCESS FOR THE PREPARATION OF DIARYLCARBONATES

This invention relates to a process for the preparation of diarylcarbonates by the reaction of phosgene with a phenol by the interface process without the addition of solvents which are immiscible with water.

It is known that an aromatic hydroxy compound can be converted into a dairyl carbonate by reaction with phosgene in the presence of a quaternary ammonium salt, e.g. tetramethylammonium iodide, at a reaction temperature above 150° C. The process can be simplified, and the yield of diaryl-carbonates improved, by reacting together an aqueous solution of an alkali metal salt of an aromatic hydroxyl compound and phosgene an adding solvent which is immiscible with water and by vigorously stirring at 25° C as described in German Patent Specification No. 1,101,386 and German Patent Specification No. 1,056,141. The first process mentioned above requires comparatively long reaction times if useful yields of diaryl carbonates are to be obtained. If the reaction is carried out in the presence of a solvent solvent losses occur and the solvents must be removed from the effluent water.

It is also known to prepare diarylcarbonates by the introduction of phosgene into an alkaline solution of o-cresol at a high pH value and elevated temperature (J.Chem.Soc. 1929, page 588). This process has the disadvantage that more than 50% of the reaction product consists of by-products, in particular phenyl chlorocarbonic acid ester (J.Chem.Soc., 1943, page 5001).

It is therefore an object of the present invention to produce diaryl carbonates with high yields substantially without the difficulties mentioned above.

It was surprisingly found that this could be achieved by a process for the preparation of symmetric diaryl carbonates by reacting phosgene with a phenol wherein said the reaction is carried out by the phase interface process in a diphasic mixture of aqueous alkali metal hydroxide solution and a liquid diaryl carbonate in the presence of from 0.001 to 0.1 mol of a tertiary amine or a quaternary ammonium compound per mol of phenol.

Particularly suitable for the reaction according to the invention is a phenol of the general formula I

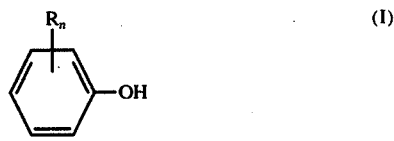

in which
R represents a hydrogen atom, an alkyl group having 1 to 4 carbon atoms, an alkoxy group having 1 to 4 carbon atoms, a phenoxy group or a halogen atom, in particular a chlorine or bromine atom,
$n$ represents an integer of from 1 to 5 and the groups R may be the same or different.

The following phenols are particularly suitable: Phenol, 2-methylphenol, 3-methylphenol, 2,4-dimethylphenol, 2-methoxphenol, 2-ethoxyphenol, 2-propoxyphenol, 2-isopropoxyphenol, 2-butoxyphenol, 2-isobutoxyphenol, 2-isoamyloxphenol, 3-butoxyphenol, 4-phenoxyphenol, 2-methoxy-4-propylphenol, 1-methyl-5-propylphenol, 2-chlorophenol, 2-bromophenol and 2-bromo-4-methylphenol.

Diarylcarbonates are obtained in particularly high yields if the reaction is carried out at a temperature of up to 30° C above the solidification point of the diaryl carbonate product and at a pH value of from 7 to 11.

In a preferred embodiment of the process according to the invention, the reaction is initially carried out at a pH value of from 7 to 9 and completed at a pH value of from 8 to 11 by adding an aqueous alkali metal hydroxide solution, preferably a 20 to 50% sodium hydroxide solution or potassium hydroxide solution during the reaction.

Phosgene is present in excess during the reaction. In particular, 1 to 1.5 and preferably 1.05 to 1.2 mol of phosgene are used per mol of phenol. At the beginning of the reaction, the proportion by weight of aqueous alkali metal hydroxide solution to diaryl carbonate is from 25:1 to 3:1. Phenol is used in qunatities of from 2 to 8 mol per liter of aqueous alkali metal hydroxide solution.

The diaryl carbonate of the diphasic reaction mixture is usually the one which is formed during the invention reaction.

The concentration of catalyst may vary within a wide range but it is preferred to use between 0.001 and 0.1 mol of the tertiary amine per mol of phenol, in particular of triethylamine, tri-n-butylamine or N,N-dimethylcyclohexylamine, or of quaternary ammonium compounds, in particular tetramethyl ammonium hydroxide or triethyl benzyl ammonium chloride.

Vigorous mixing must be maintained throughout the reaction time. This is generally achieved by using high speed mechanical stirrers or by vigorously circulating the reaction mixture through turbine pumps which have a powerful turbulent delivery action.

As already mentioned above, according to the particularly preferred embodiment of the process of the invention, the reaction is carried out in two stages. By carrying out phosgenation initially at lower pH values in the presence of the catalyst, the corresponding chlorocarbonic acid esters are formed very rapidly. But suprisingly they do not undergo saponification in spite of amine catalysis. Increasing then the pH by at least one unit accelerates the formation of carbonate greatly. As a general rule, after the phosgenation of the first stage, the reaction is completed in about 1 to 30 minutes at a pH value which is at least one unit higher.

The pH value at the beginning of the reaction depends on the phenols used, because we found that the more acid the phenol used is the lower should be the pH value for both reaction stages. The pH value, however should preferably be raised by at least one unit in the second stage of the reaction.

According to a preferred embodiment of the invention, the diarylcarbonates are prepared continuously in a pump circulation reactor. The reactor consists of a coil provided with a heat exchanger and dosing devices for the aqueous alkali metal phenolate solution, phosgene, aqueous alkali metal hydroxide solution and catalyst. An appropriate quantity of diaryl carbonate is introduced into the reactor. The first components to be fed into the reactor are the alkali metal phenolate solution and the catalyst, which are introduced together on the upstream side of the delivery pump, followed by diaryl carbonate and then phosgene and finally an additional quantity of alkali metal hydroxide solution to adjust the reaction mixture to the required pH. The intervals at which the various components are introduced should be calculated to ensure that each component has been already in the reactor for at least one second before the next is added. These brief reaction times between the introduction of the individual components are sufficient to bring about preferential reaction of the phosgene with the alkali metal salt of phenol in a first reaction phase without substantial proportions of phosgene undergoing a saponification reaction with the aqueous alkali metal hydroxide solution. The delay in the supply of the additional alkali metal hydroxide solution prevents the occurrence of localised high hydroxyl group concentrations during the required primary reaction and hence prevents saponification of the diarylcarbonate added with the formed chlorocarbonic acid ester, which would reduce the yield. For the second reaction stage, the reaction mixture is left to react to completion in a cascade of stirrer vessels.

The diarylcarbonates are generally obtained in form of melts. They can be isolated by the known methods for separating two immiscible liquids, for example by phase separation in separators followed by washing with hot water to remove the inorganic salts. Another possible method for isolating the diarylcarbonates is cooling the reaction mixture to a temperature below the melting point of the diarylcarbonate and filtering the crystallised product and washing it with water.

The process according to the invention may in principle be used for the preparation of diarylcarbonates with melting points either below or above 100° C but it is preferably used for the preparation of diaryl carbonates which have a melting point below 100° C, because the inventive process can then be carried out at normal pressure. To prepare diarylcarbonates with a melting point above 100° C, it is necessary to employ elevated pressure or to carry out only partial phosgenation and use the unreacted phenol for lowering the melting point.

The process according to the invention is carried out without the addition of a with water immiscible solvent because the diarylcarbonate put into the process and that produced during the reaction forms the necessary second phase for carrying out the process. This and the control of pH ensure that phosgene saponification and saponification of the arylchlorocarbonic acid ester which is formed as intermediate product occur only to a very minor extent. Phosgene and the arylchlorocarbonic acid ester preferentially react with the alkali metal phenolate present, even at the high temperatures employed, rather than undergo saponification.

The diarylcarbonates prepared according to the invention are used for the preparation of polycarbonates by the known transesterification process. In this process, aromatic dihydroxy compounds are reacted with diarylcarbonates in a solvent-free reaction mixture in the presence of small quantities of alkali. The given phenol split off in the reaction and high molecular weight polycarbonates are formed.

EXAMPLE 1 a. 94 Parts of phenol are mixed with 200 parts of water in a three-necked flask equipped with stirrer, dropping funnel and gas inlet and gas discharge tube. When the air in the flask has been replaced by nitrogen, the mixture is heated to 85° C, 21 parts of diphenylcarbonate are added, the reaction mixture is adjusted to pH 8 with 45% sodium hydroxide solution, and 0.25 parts of 4% aqueous triethylamine are added. 54.5 Parts of phosgene are then introduced with vigorous stirring over a period of 30 minutes and at the same time the pH is kept at 8 by the addition of 45% sodium hydroxide solution. After the introduction of phosgene has been terminated, the reaction mixture is kept at 85° C and pH 10 for a further 10 minutes under stirring. It is then cooled until diphenylcarbonate separates as a solid. The solid is filtered off and the filter residue is thorougly washed with water. The yield of crude product was 106 parts (99%) (based on the quantity of phenol), with a melting point of 70° C.

b. A mixture of 45.6 parts by weight of 2,2-(4,4'-dioxydiphenyl)-propane, 47.1 parts by weight of the diphenyl carbonate prepared according to (a) and 0.008 parts by weight of lithium hydride is melted at 110° to 150° C in a nitrogen atmosphere under stirring. The phenol which splits off in the reaction is distilled off by further increase of temperature up to 210° C at a pressure of 20 Torr. The pressure is then reduced to 0.2 Torr and the temperature raised to 250° C during 1 hour and to 280° C during 2 further hours. Towards the end of condensation, the catalyst is neutralised by stirring 0.05 parts by weight of dimethylsulphate into the melt. The excess of neutralising agent is then removed by further heating under vacuum. A highly viscous melt which solidifies to a thermoplastic resin softening at about 225° C and melting at 240° C is obtained. It can be used, for example, for the manufacture of injection moulded articles and of fibres which can be orientated by stretching, bristles and films from the melt or from solutions, e.g. in methylene chloride. The K-value, determined in m-cresol is 51. The solvent-free, molten products are stable at processing temperatures of up to and over 300° C without decomposition or elimination of carbon dioxide. Shaped products produced from the melt are capable of withstanding elevated temperatures for prolonged periods, even in the presence of water.

EXAMPLES 2 to 7.

Various phenols are reacted with phosgene in the same procedure as described in Example 1. The results are summarised in Table I.

Table I

| Example | Phenol | pH 1st Reaction Stage | pH 2nd Reaction Stage | Reaction temperature ° C | Yield % | M.p. found ° C | M.p. according to the literature ° C | Saponifiable Cl ppm |
|---|---|---|---|---|---|---|---|---|
| 1 | Phenol | 8 | 10 | 80–85 | 99 | 79 | 79.5 | <10 |
| 2 | 2-Methylphenol | 9 | 10.5 | 75–80 | 90 | 53 | 57 | 30 |
| 3 | 3-Methylphenol | 9 | 10 | 65–70 | 95 | 49 | 51 | 45 |
| 4 | 2,4-Dimethylphenol | 9 | 10.5 | 65–70 | 82 | 45 | 47 | 20 |
| 5 | 2-methoxyphenol | 9 | 11 | 90–95 | 92 | 84 | 89 | 70 |
| 6 | 4-Methoxyphenol | 8 | 10 | 90–95 | 85 | 92–93 | 93 | <10 |

Table I-continued

| Example | Phenol | pH 1st Reaction Stage | pH 2nd Reaction Stage | Reaction temperature °C | Yield % | M.p. found °C | M.p. according to the literature °C | Saponifiable Cl ppm |
|---|---|---|---|---|---|---|---|---|
| 7 | 2-chlorophenol | 7.5 | 9 | 75–80 | 99 | 64 | 55+ | 25 |

+German Patent 81 375, Beilstein 6, page 185
Elementary analysis of the compound: $C_{13}H_8Cl_2O_3$
Found: C 55.1% H 2.44% Cl 24.7%
Calculated: C 55.2% H 2.82% Cl 25.1%
M.p. = melting point

EXAMPLE 8

The following streams of products are fed into a pump circulation reactor of the kind described on page 4 which has a reaction volume of 0.8 liters:
1. 3.760 kg/hour of a sodium phenolate solution of the following composition:
   1.128 kg of phenol
   1.565 kg of water
   1.067 kg of 45% sodium hydroxide solution
   0.12 g of triethylamine
2. 0.683 kg/hour of phosgene
3. 0.3 kg/hour of 45% sodium hydroxide solution
4. 2.539 kg/hour of water.

The reaction temperature is 89° C, the pH 8.5. When the quantities indicated above are pumped into the reactor, the average time of stay of the reactants is 7.2 minutes.

0.025 kg/hour of 45% aqueous sodium hydroxide solution is added to the reaction emulsion discharge from the pump circulation reactor in order to increase its pH to 9.5, and the emulsion is then passed through a cascade of stirrer vessels (2 vessels each with a capacity of 1 liter). The average time of stay is 18 minutes, the temperature 87° C.

The phases are separated in a settling tank and the diphenylcarbonate phase is washed with 0.6 l/hour of water in a mixer separator at 85° C.

The diphenylcarbonate is distilled under vacuum at 190° C/23 mm Hg.
M.p. 79° C.
Yield: 1.245 kg/hour, corresponding to 97% of the theory, based on the quantity of phenol put into the reaction.

What we claim is:

1. A process for preparing a symmetrical diarylcarbonate which comprises reacting phosgene and phenol in the phase interface process in a diphastic mixture of aqueous alkali metal hydroxide solution and a liquid diarylcarbonate in the presence of from 0.001 to 0.1 mol of a tertiary amine or a quaternary ammonium compound, per mol of phenol and at a temperature of up to 30° C. above the solidification point of the diarylcarbonate and at a pH of from 7 to 11.

2. A process as claimed in claim 1 wherein the phenol is a phenol of the formula:

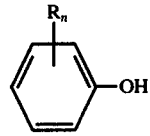

in which
R represents a hydrogen atom, an alkyl group, an alkoxy group, a phenoxy group or a halogen atom,
n represents an integer of from 1 to 5 and the groups R may be the same or different.

3. A process as claimed in claim 1 wherein the reaction is initially carried out at a pH of from 7 to 9 and is completed at a pH of at least one unit higher and from 8 to 11 by the addition of aqueous alkali metal hydroxide solution to the reaction mixture.

4. A process as claimed in claim 1 wherein 1 to 1.5 mol of phosgene are used per mol of phenol.

5. A process as claimed in claim 4 wherein from 1.05 to 1.2 mol of phosgene are used per mol of phenol.

6. A process as claimed in claim 1 wherein at the beginning of the reaction proportion by weight of aqueous alkali metal hydroxide solution to diaryl carbonate is from 25 : 1 to 3 : 1.

7. A process as claimed in claim 1 wherein the initially employed diarylcarbonate corresponds to the diarylcarbonate product of the process.

8. A process as claimed in claim 1 wherein the phenol is used in a quantity of from 2 to 8 mol per liter of aqueous alkali metal hydroxide solution.

9. A process as claimed in claim 1 wherein from 0.001 to 0.1 mol of tertiary amine or quaternary ammonium compound are used per mol of phenol.

10. A process as claimed in claim 1 wherein the tertiary amine is triethylamine, tri-n-butylamine or N,N-dimethylcyclohexylamine.

11. A process as claimed in claim 1 wherein the quaternary ammonium compound is tetramethyl ammonium hydroxide or triethyl benzyl ammonium chloride.

12. A process as claimed in claim 1 wherein the diaryl carbonate is continuously prepared in a pump circulation reactor.

13. A process as claimed in claim 1 wherein the diaryl carbonate initially employed has a melting point below 100° C.

* * * * *